United States Patent [19]

Kaufhold

[11] Patent Number: 5,763,627
[45] Date of Patent: Jun. 9, 1998

[54] PROCESS FOR PREPARING CYCLOPROPYL ALKYL KETONES AND 4,5-DIHYDROALKYFURANS

[75] Inventor: Manfred Kaufhold, Marl, Germany

[73] Assignee: Huels Aktiengesellschaft, Marl, Germany

[21] Appl. No.: 881,937

[22] Filed: Jun. 25, 1997

[51] Int. Cl.$^6$ .............. C07C 45/54; C07D 307/78
[52] U.S. Cl. .............. 549/507; 568/314; 568/343; 568/346
[58] Field of Search .............. 549/507; 568/343, 568/314, 346

[56] References Cited

U.S. PATENT DOCUMENTS 5,629,455  5/1997  Kaufhold .............. 568/343

*Primary Examiner*—Patricia L. Morris
*Assistant Examiner*—Raymond Covington
*Attorney, Agent, or Firm*—Oblon, Spivak, McClelland, Maier & Neustadt, P.C.

[57] ABSTRACT

The invention relates to a novel process for simultaneously preparing cyclopropyl alkyl ketones and 4,5-dihydroalkylfurans from 3-acyltetrahydrofuran-2-ones in the presence of a metal salt according to the scheme

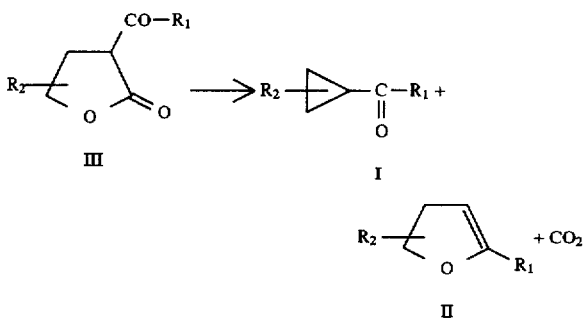

during the reaction. high-boiling poly (ethylene glycol) dialkyl ethers are then used. By introducing the solvent, the metal salt and the 3-acyltetrahydrofuran-2-one in a molar excess to the metal salt, heating the mixture to 160° to 220° C. and adding further 3-acyltetrahydrofuran-2-one, the desired products are obtained in high yields. The metal salt can, moreover, be recovered in a simple manner by washing with water.

16 Claims, No Drawings

PROCESS FOR PREPARING CYCLOPROPYL ALKYL KETONES AND 4,5-DIHYDROALKYFURANS

BACKGROUND OF THE INVENTION

1. Field of the Invention

The invention relates to a novel process for simultaneously preparing cyclopropyl alkyl ketones of the formula I and 4,5-dihydroalkylfurans of the formula II from 3-acyltetrahydrofuran-2-ones of the formula III according to the scheme:

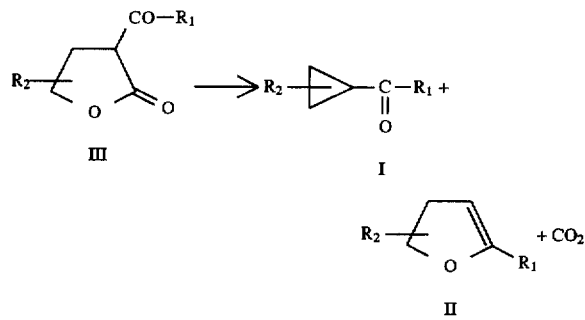

In this reaction scheme, $R_1$ is $C_{1-4}$ alkyl, cyclohexyl or phenyl and $R_2$ is hydrogen, $C_{1-4}$ alkyl or phenyl. This reaction proceeds in the presence of a metal salt in a high-boiling solvent at 160° to 220° C.

2. Discussion of the Background

Compounds of the formulae I and II are known. They serve as important starting compounds for preparing plant-protection compositions and pharmaceutical products. The preparation of cyclopropyl alkyl ketones from 3-acyltetrahydrofuran-2-ones by decarboxylation reactions is disclosed in the literature. Thus, for the reaction according to Takei, Tetrahedron Letters No. 49, 4389–92 (1975), a 10% molar excess of alkali metal halide, based on the substrate, and, furthermore, a polar solvent, such as dimethyl sulfoxide or dimethylformamide, are always employed. In this process, the recovery of the large amounts of alkali metal halide is particularly complex, since both the metal salt and the solvent are highly water-soluble.

In Asaoka, Chemistry Letters 11, 1149–52 (1975), α-acetyl-γ-butyrolactone is reacted with a deficiency of NaI in hexamethylphosphoric triamide (HMPA), a further highly polar solvent. After distillation of the cyclopropyl methyl ketone, the recovery of the metal salt from the polar solvent also requires a complex work-up process.

According to EP-A-0 610 819, good yields are only obtained using HMPA, with the solvent being said to be expensive and not harmless. In addition, a gas-phase reaction on a catalyst bed is subject matter of this application. However, the gas-phase reaction requires special equipment. Furthermore, it is associated with great technical complexity, since the catalyst must first be prepared on a solid support and must later be regenerated or disposed of.

In EP-A-0 552 586, a large excess of a halide is introduced in a polar solvent, generally N-methylpyrrolidone, whereupon acetylbutyrolactone is added dropwise at the reaction temperature and cyclopropyl methyl ketone is distilled. Recovery of the metal salt is absolutely necessary in this process, because of the large amount of metal salt and for environmental protection reasons. Recovery in this case also is highly complex.

The object of the present invention is to provide a simple process which may be carried out in conventional stirring equipment in which the catalyst can be recovered in a simple manner and in which only a small amount of high-boiling waste products are formed.

SUMMARY OF THE INVENTION

The object is achieved according to the invention by reacting a 3-acyltetrahydrofuran-2-one of the formula III with a metal salt to form a cyclopropyl alkyl ketone of the formula I and a 4,5-dihydroalkylfuran of the formula II, using as a solvent for the reaction a poly(ethylene glycol) dialkyl ether of the formula IV

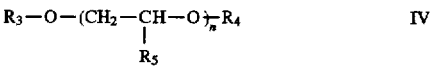

In this formula, $R_3$ and $R_4$ are each independently $C_{1-4}$ alkyl radicals, $R_5$ is hydrogen or a methyl group, and n is an integer from 20 to 50. The reaction is carried out in a manner such that the metal salt and a portion of 3-acyltetrahydrofuran-2-ones of the formula III, in a molar excess to the metal salt, are introduced into the solvent, heated to 160° to 220° C., then further III is added, and I and II are distilled off in the course of this.

DETAILED DESCRIPTION OF THE PREFERRED EMBODIMENTS

Non-limiting examples of cyclopropyl alkyl ketones I which may be prepared according the the present invention are cyclopropyl methyl ketone, cyclopropyl ethyl ketone, cyclopropyl phenyl ketone, cyclopropyl cyclohexyl ketone and 1-methylcyclopropyl phenyl ketone.

Non-limiting examples of 4,5-dihydroalkylfurans II are 4,5-dihydro-2-methylfuran, 4,5-dihydro-2,5-dimethylfuran, 4,5-dihydro-2-phenylfuran, 4,5-dihydro-2-cyclohexylfuran and 4,5-dihydro-5-methyl-2-phenylfuran.

Non-limiting examples of suitable starting compounds III are, for example, α-acetyl-γ-butyrolactone, 3-acetyl-5-methyltetrahydrofuran-2-one, α-benzoyl-γ-butyrolactone, α-acetyl-α-phenyl-γ-butyrolactone and α-benzoyl-α-methyl-γ-butyrolactone.

Non-limiting examples of suitable metal salts are especially alkali metal halides and alkaline earth metal halides, alkali metal halides being preferably used. Examples of these are LiBr, LiI, KCl, NaBr, KBr, NaI and KI, NaI and KI being very particularly preferred.

Metal salt and 3-acyltetrahydrofuran-2-one of the formula III are introduced into the solvent, preferably in a molar ratio of metal salt to 3-acyltetrahydrofuran-2-one of the formula III of 1:1 to 1:10, more preferably in a molar ratio of 1:2.5 to 1:5, and even more preferably about 1:2.

The solvent IV is a high-boiling, polar, water-soluble compound. Non-limiting examples of these are poly(ethylene glycol) dimethyl ether, poly(ethylene glycol) diethyl ether, poly(propylene glycol) dimethyl ether and a mixture thereof.

Because of its high boiling point, the solvent enables simple recycling of the metal salt from the high-boilers produced as by-product, since the metal salt can be extracted with water, together with the solvent, and then the water of the extract can be distilled off. The solvent IV remaining in the bottom phase then dissolves the metal salt present in the anhydrous state.

The solvent can be used in pure form. It can alternatively be replaced by up to 50%, based on the total amount of solvent, by high-boiling, polar, water-soluble solvents, such as dimethylformamide, dimethyl sulfoxide or N-methylpyrrolidone.

It is essential for the process of the invention that 3-acyltetrahydrofuran-2-one III is introduced in a molar excess to the metal salt. This is shown by the experimental data. With this excess, the products I and II can then be prepared surprisingly simply and economically using the special solvents.

In contrast to the opinion expressed in EP-A-0 610 819, high yields are also achieved with the less polar solvents. As a difference from the prior art, high-boiling products are only formed in small amounts. Instead, it is produced as a further low-boiling product. The small amounts of high-boilers have the economic advantage that the bottom phase needs to be worked up less frequently and that therefore the time in service, until the reaction is terminated, is increased.

Less salt is used, which is recovered less frequently, and in a simple manner. At the same time, with II, a further valuable intermediate is obtained. To carry out the process of the invention, the solvent or a solvent mixture and III are introduced and the metal salt is then added thereto. The concentration of the metal salt is generally 5 to 20% by weight, based on the mixture of solvent and III. In particular, a molar ratio of metal salt and III of 1:2 is set. The mixture is heated to 160° to 220° C., preferably 180° to 200° C. and further III is added. I and II then forming are distilled off.

The following examples are intended to illustrate the invention.

COMPARISON EXAMPLE A

Into glass equipment comprising a three-necked flask equipped with agitator, thermometer, distillation column, bridge-shaped stillhead and receiver, the following are introduced:

100 g of 1-(N-octyl)caprolactam (NOC)

40 g (0.31 mol) of 3-acetylbutyrolactone (ABL)

15 g (0.1 mol) of NaI, anhydrous.

The products are mixed and heated to 180° C., in the course of which no distillate is produced.

EXAMPLE 1

The equipment described in Comparison Example A is used and the following are introduced:

300 g of poly(ethylene glycol) dimethyl ether 2000 (poly(ethylene glycol) M=2000, capped at both ends with methyl groups), 30 g of NaI (0.2 mol) and 60 g of 2-acetyl-γ-butyrolactone (0.47 mol). The mixture is then heated to 175°–180° C.

At the same time, continuous metering of 2-acetyl-γ-butyrolactone is started, 60 g/h (0.47 mol) being transported by a metering pump. In accordance with the amount of starting material, approximately 40 g of crude cyclopropyl methyl ketone and approximately 10 L of $CO_2$ are formed per hour.

After purification of this crude mixture by distillation, 34.5 g of cyclopropyl methyl ketone (99% pure) are obtained, based on the 0.47 mol of 2-acetyl-γ-butyrolactone metered in per hour, which corresponds to a yield of approximately 87% (of theory).

Obviously, numerous modifications and variations of the present invention are possible in light of the above teachings. It is therefore to be understood that within the scope of the appended claims, the invention may be practiced otherwise than as specifically described herein.

This application is based on German Patent Application DE-196 30 449.0, filed in the German Patent Office on Jul. 27, 1996, the entire contents of which are hereby incorporated by reference.

What is claimed as new and desired to be secured by Letters Patent of the United States is:

1. A process for simultaneously preparing cyclopropyl alkyl ketones of the formula I and alkyl-4,5-dihydro-2-alkylfurans of the formula II from 3-acyltetrahydrofuran-2-ones of the formula III

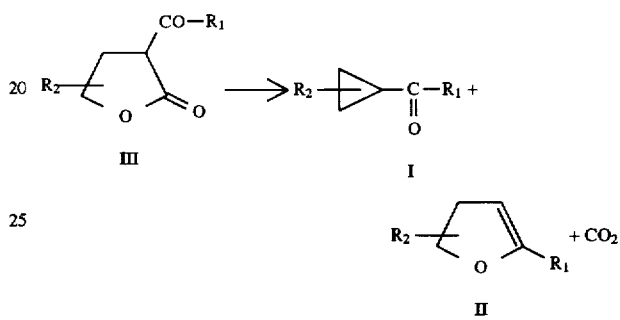

where $R_1 = C_{1-4}$ alkyl, cyclohexyl or phenyl and $R_2 = H$, $C_{1-4}$ alkyl or phenyl, comprising reacting a metal salt and 3-acyltetrahydrofuran-2-one III, in a molar excess to the metal salt, in a solvent comprising a poly(ethylene glycol) dialkyl ether of the formula IV

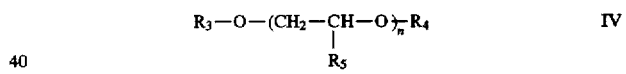

where $R_3$, $R_4$ are each independently $C_{1-4}$ alkyl $R_5 = H$ or methyl and n=20 to 50, heating the mixture to 160° to 220° C., then adding further 3-acyltetrahydrofuran-2-one of the formula III and distilling off cyclopropyl alkyl ketone of formula I and alkyl-4,5-dihydro-2-alkylfuran of formula II in the course of this.

2. The process of claim 1, wherein said metal salt used is an alkali metal halide.

3. The process of claim 2, wherein said metal salt is selected from the group consisting of NaI, KI and a mixture thereof.

4. The process of claim 1, wherein said metal salt and III are introduced in a molar ratio of 1:2 to 1:10.

5. The process of claim 1, said metal salt and 3-acyltetrahydrofuran-2-ones of the formula III are introduced in a molar ratio of 1:2.5 to 1:5.

6. The process of claim 1, further comprising recovering said metal salt by washing with water, after the distillation of cyclopropyl alkyl ketone of formula I and alkyl-4,5-dihydro-2-alkylfuran of formula II.

7. The process of claim 1, wherein said solvent IV further comprises up to 50% by weight of a high-boiling, polar, water-soluble solvent, based on the total amount of solvent.

8. The method of claim 1, wherein said 3-aceytetrahydrofuran-2-one of formula III is selected from the group consisting of α-acetyl-γ-butyrolactone, 3-acetyl-5-methyltetrahydrofuran-2-one, α-benzoyl-γ-butyrolactone, α-acetyl-α-phenyl-γ-butyrolactone and α-benzoyl-α-methyl-γ-butyrolactone.

9. The method of claim 1, wherein said cyclopropyl alkyl ketone of formula I is selected from the group consisting of cyclopropyl methyl ketone, cyclopropyl ethyl ketone, cyclopropyl phenyl ketone, cyclopropyl cyclohexyl ketone and 1-methylcyclopropyl phenyl ketone.

10. The method of claim 1, wherein said 4,5-dihydroalkylfuran of formula II is selected from the group consisting of 4,5-dihydro-2-methylfuran, 4,5-dihydro-2,5-dimethylfuran, 4,5-dihydro-2-phenylfuran, 4,5-dihydro-2-cyclohexylfuran and 4,5-dihydro-5-methyl-2-phenylfuran.

11. The method of claim 1, wherein said poly(ethylene glycol)dialkyl ether of formula IV is selected from the group consisting of poly(ethylene glycol) dimethyl ether, poly (ethylene glycol) diethyl ether, poly(propylene glycol) dimethyl ether and a mixture thereof.

12. The method of claim 1, wherein said metal salt is selected from the group consisting of alkali metal halides, alkaline earth metal halides and a mixture thereof.

13. The method of claim 1, wherein said metal salt is selected from the group consisting of LiBr, LiI, KCl, NaBr, KBr, NaI, KI and a mixture thereof.

14. The method of claim 1, wherein a concentration f of said metal salt is 5 to 20% by weight based on said mixture of solvent and 3-acyltetrahydrofuran-2-one of formula III.

15. The method of claim 1, wherein heating said mixture is from 180° to 200° C.

16. The method of claim 7, wherein said high-boiling, polar, water-soluble solvent is selected from the group consisting of dimethylformamide, dimethyl sulfoxide, N-methylpyrrolidone and a mixture thereof.

* * * * *